United States Patent [19]
Gosselin et al.

[11] Patent Number: 5,770,725
[45] Date of Patent: Jun. 23, 1998

[54] PHOSPHOTRIESTER TYPE BIOLOGICALLY ACTIVE COMPOUNDS

[76] Inventors: Gilles Gosselin, Résidencé "Parc-des-Arceaux", Bât. F1, Rue Paul-Rimbaud - 34000 Montpellier; Jean-Louis Imbach, Laboratoire de Chimie Bio Organique USTL, Place Eugène Bataillon - 34095 Montpellier, both of France

[21] Appl. No.: 416,515

[22] Filed: Apr. 4, 1995

Related U.S. Application Data

[63] Continuation-in-part of Ser. No. 343,433, PCT/FR93/00498 May 24, 1993, abandoned.

[30] Foreign Application Priority Data

May 25, 1992 [FR] France .................................. 92 06383
Apr. 7, 1993 [FR] France .................................. 93 04117

[51] Int. Cl.$^6$ .............................. C07H 1/00; C07H 19/00
[52] U.S. Cl. ................. 536/26.7; 536/26.71; 536/26.72; 536/26.74; 536/26.8; 536/26.9; 544/243; 544/264
[58] Field of Search ................................. 536/26.8, 26.7, 536/26.71, 16.72, 26.74, 26.9; 544/243, 264

[56] References Cited

U.S. PATENT DOCUMENTS 5,430,136 7/1995 Urdea et al. ............................ 536/243
5,430,138 7/1995 Urdea et al. ........................... 536/26.8

FOREIGN PATENT DOCUMENTS

| | | |
|---|---|---|
| 0 217 580 | 4/1987 | European Pat. Off. |
| 0 322 384 | 6/1989 | European Pat. Off. |
| 0 481 214 | 9/1991 | European Pat. Off. |
| 2 654 106 | 5/1991 | France . |
| WO 90/08155 | 7/1990 | WIPO . |
| WO 91/14696 | 3/1991 | WIPO . |
| WO 91/19721 | 12/1991 | WIPO . |

OTHER PUBLICATIONS

Hao, Z. et al., "Potent DNA Chain Termination Activity and Selective Inhibition of Human Immunodeficiency Virus Reverse Transcriptase by 2', 3'—Dideoxyuridine–5'-triphosphate", *Molecular Pharmacology* 1990, 37, 157–163.

Hao, Z. et al, "2', 3'–Dideoxyuridine Triphosphate: A Potent Inhibitor of HIV Reverse Transcriptase", *Proceedings of AACR* 1988, 29, 348.

Matthes, E. et al., "Inhibition of HIV–Associated Reverse Transcriptase By Sugar–Modified Derivatives of Thymidine 5'–Triphosphate in Comparison to Cellular DNA Polymerases α and β", *Biochemical and Biophysical Research Communications* 1997, 148(1), 78–85.

Rosenberg et al., "Synthesis of Potential Prodrugs and Metabolites of 9–(S)–(3–Hydroxy–2–Phosphonylmethoxypropyl)Adenine", *Collection Czechoslovak Chem. Comm.* 1987, 52, 2792–2800.

*Primary Examiner*—James O. Wilson
*Attorney, Agent, or Firm*—Woodcock Washburn Kurtz Mackiewicz & Norris LLP

[57] ABSTRACT

Compounds of formula RO—P(=O)(OR)—Nu where: each R is, independently, —(CH$_2$)$_n$—S—X; X is —C(=Z) (Y) or —S—U; Z is O or S; Y and U are alkyl, aryl or saccharide groups optionally substituted with OH, SH or NH groups; n is 1 to 4; and Nu is a nucleoside which comprises a ribose or deoxyribose sugar portion covalently bound to a base portion.

13 Claims, 6 Drawing Sheets

FIG_1

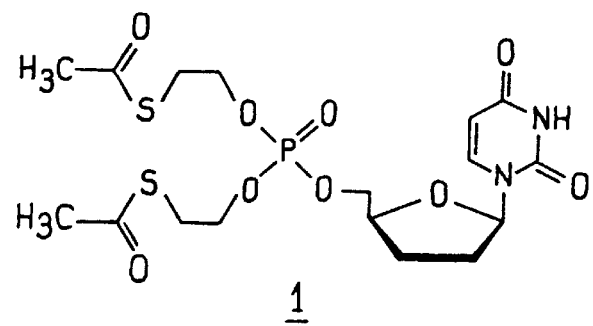
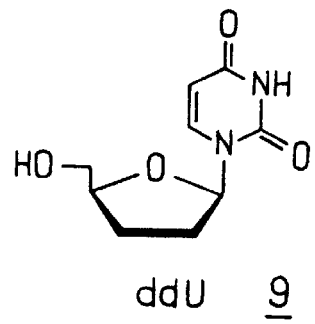
ddU  9
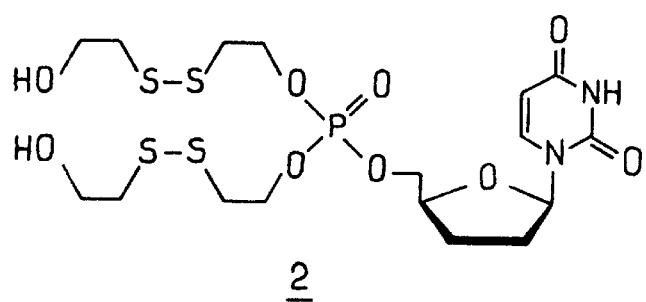
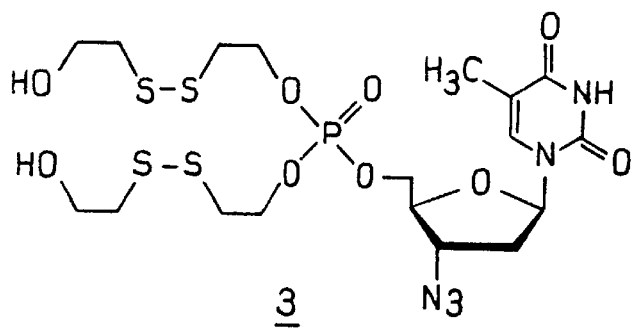
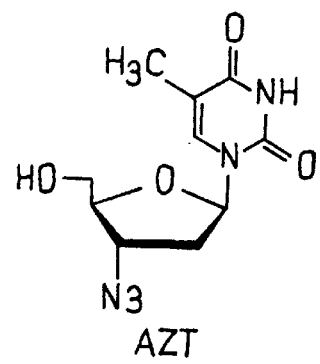
AZT
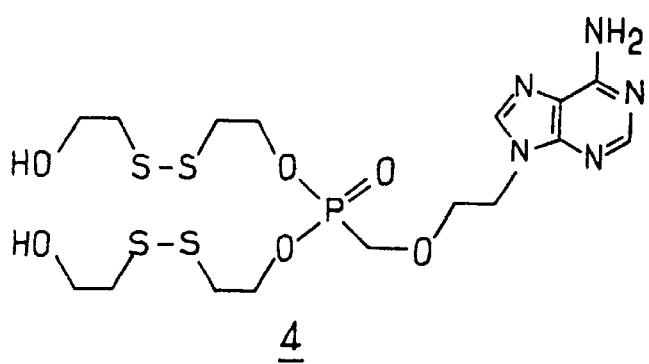
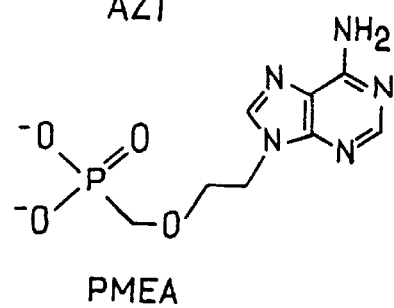
PMEA
FIG_3

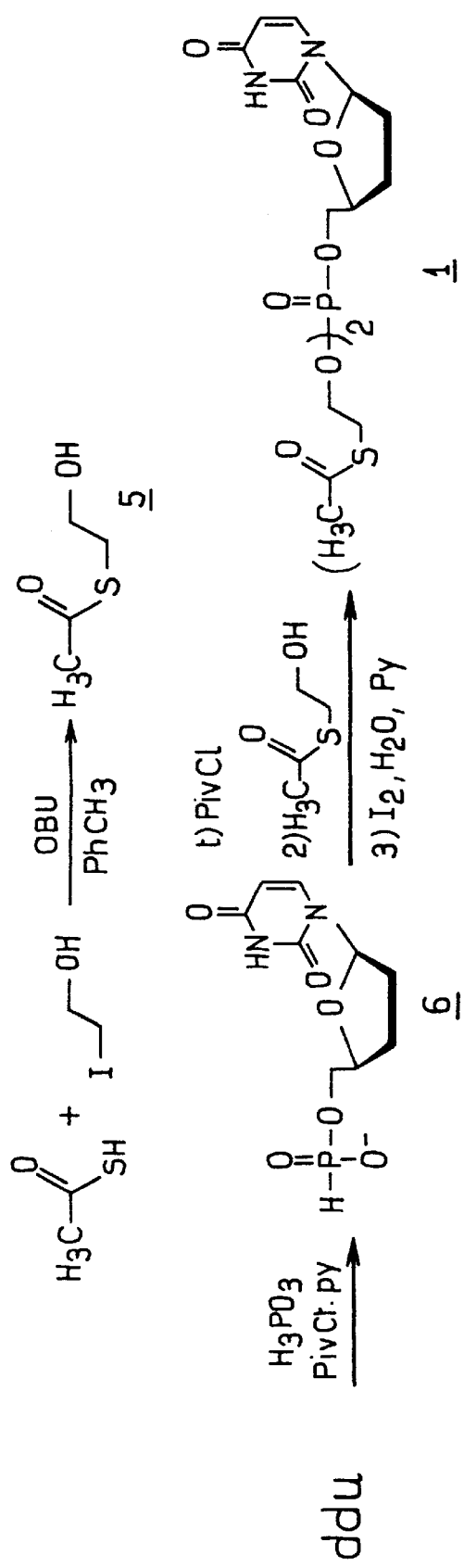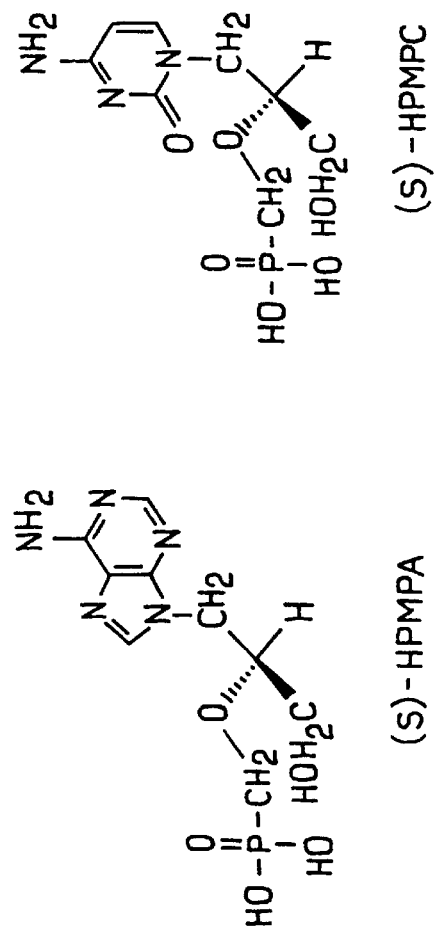
FIG_4

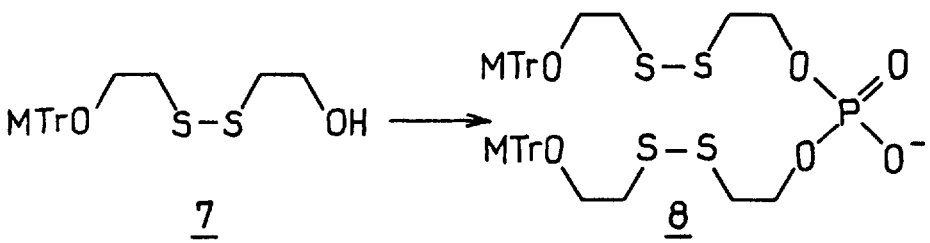
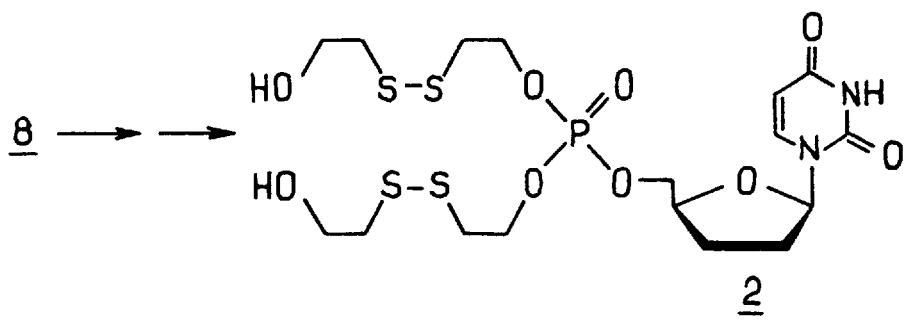
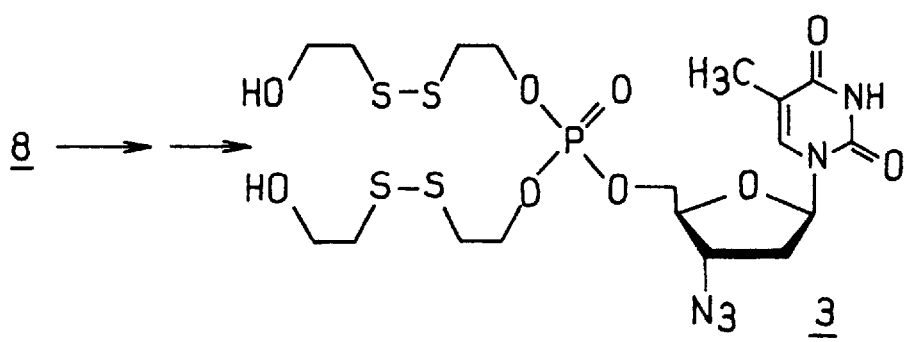
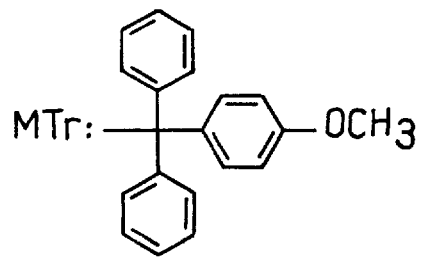
FIG. 5

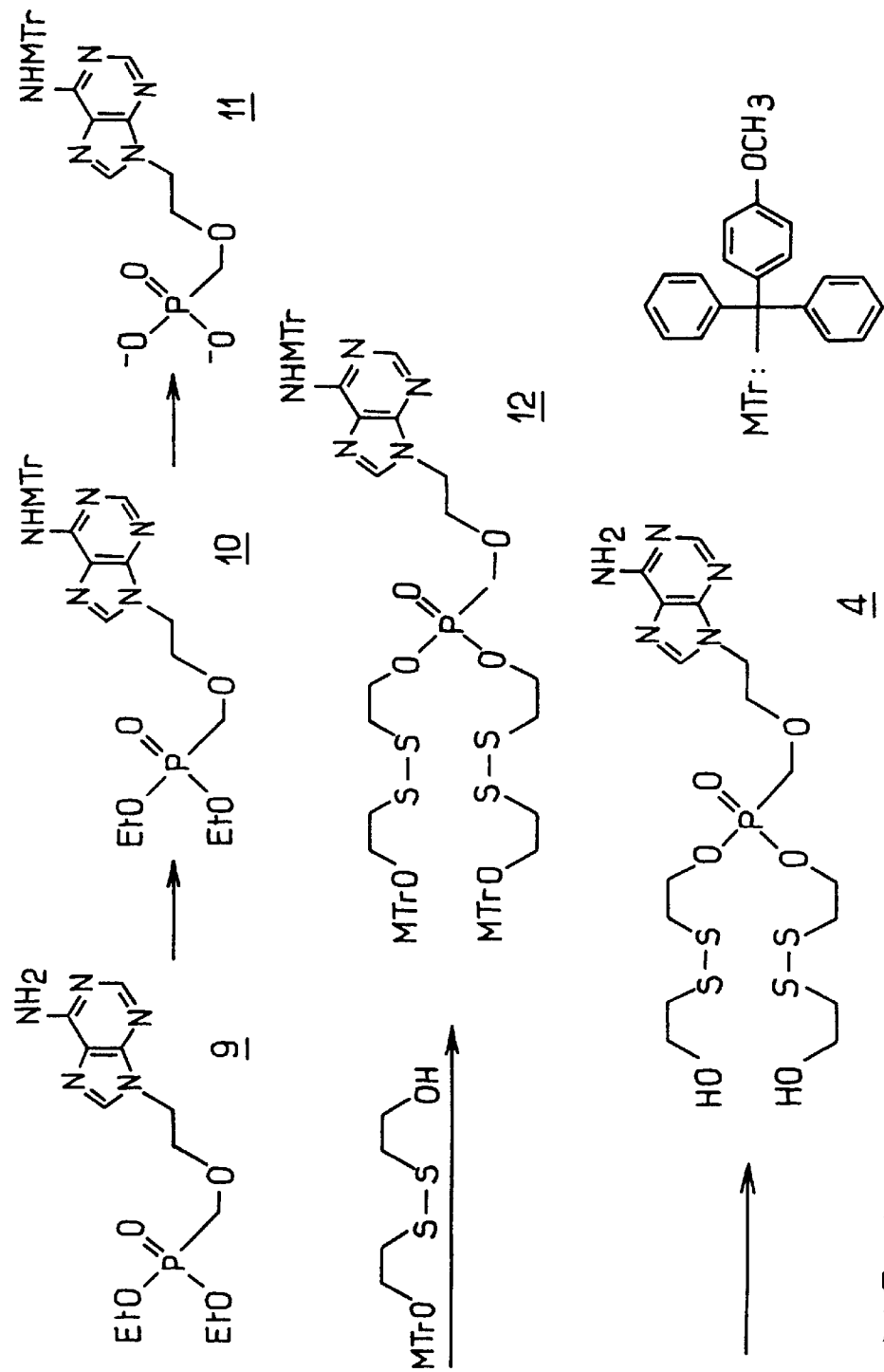
FIG._6

PHOSPHOTRIESTER TYPE BIOLOGICALLY ACTIVE COMPOUNDS

This is a continuation-in-part of application Ser. No. 08/343,433, filed on Nov. 23, 1994, now abandoned, which is a U.S. designation of PCT/FR93/00498 filed on May 24, 1993.

The present invention relates to the bioreversible functionalization of phosphate or phosphonate groups of biologically active compounds.

The present invention relates more particularly to phosphotriester-type biologically active compounds bearing phosphate or phosphonate groups which are protected by protecting groups that are bioreversible in an intracellular medium.

Compounds bearing a phosphate or phosphonate group have a negatively charged ionic nature and a physiological pH. As a result, the therapeutic activity of such compounds is limited by the low diffusion of negatively charged compounds across biological lipid membranes. Moreover, compounds bearing phosphate groups are readily dephosphorylated by the action of phosphatase enzymes in the blood or on cell membranes, which enzymes dephosphorylate substrate compounds. In general, charged phosphate or phosphonate compounds are poorly absorbed via oral administration, and do not diffuse efficiently across cell membranes or even the cerebral barrier, which are lipidic in nature.

Certain compounds, such as nucleoside derivatives or analogs, are active agents that are administered in non-phosphorylated form, but are phosphorylated in vivo in the form of metabolic monophosphate or triphosphate to become active.

Thus, nucleoside derivatives having antitumor activity, such as 5-fluorouridine, 5-fluoro-2'-deoxyuridine or 1-β-D-arabinofuranosylcytosine, exert their activity in phosphorylated form.

Similarly, in order to exert their anti-proliferative activity, certain nucleoside or phosphononucleoside analogs need to be phosphorylated into the corresponding triphosphate thereof by cellular or viral enzymes; this triphosphate is then capable of inhibiting the viral and/or cellular polymerases.

Among the various structural classes of antiviral agents, 2',3'-dideoxynucleosides are among the most effective compounds in the treatment of AIDS. However, these nucleoside analogs must undergo a biotransformation by cell kinases in order to exert their activity on the replication of HIV, the etiological agent of AIDS. This metabolization occurs via the dideoxynucleoside 5'-monophosphate and then the 5'-diphosphate to lead to the 5'-triphosphate, which is an inhibitor of HIV reverse transcriptase and which thereby interferes with the biosynthesis of viral DNA.

Despite their great therapeutic potential, 2',3'-dideoxynucleosides suffer from limitations, in particular the low metabolizability of some of them by kinases into triphosphate. 2',3'-Dideoxyuridine 5'-triphosphate, for example, is an excellent inhibitor of reverse transcriptase (Z. Hao et al., Proc. Am., Assoc. Cancer Res., 1988, 29, 348, E. Matthes et al., Biochem. Biophys. Res. Commun, 1987, 148, 78–85). However, the nucleoside thereof is unable to inhibit the replication of HIV in vitro. Studies have shown that this result is linked to the low metabolizability of the nucleoside into its monophosphate by cell kinases (Z. Hao et al. Mol. Pharmacol. 1990, 37, 157–153).

Thus, AZT is successively metabolized into the triphosphate thereof (AZTP), which is a potent inhibitor of HIV reverse transcriptase. Similarly, Acyclovir (ACV) is converted into the triphosphate thereof (ACVTP), which selectively inhibits herpesvirus DNA polymerase. The first step in the activation of the nucleosides (Nu) consists of a monophosphorylation, leading to the corresponding monophosphate (NuMP). It is this first step which is the most selective.

In order to circumvent this key step of enzymatic monophosphorylation, it has already been proposed to adminster NuMPs directly, but their use for therapeutic purposes was contraried by the abovementioned limitations and drawbacks.

Compounds bearing a phosphate or phosphonate group have a negatively charged ionic nature at physiological pH. The therapeutic activity of such compounds is consequently limited, on account of the low diffusion of negatively charged compounds across biological lipid membranes. In particular, charged compounds do not diffuse efficiently across cell membranes, or indeed across the cerebral barrier, which are lipidic in nature. Moreover, such compounds are readily dephosphorylated by the action of phosphatase enzymes in the blood or on the cell membranes, which enzymes dephosphorylate the substrate compounds thereof. In general, charged phosphate or phosphonate compounds are poorly absorbed via oral administration.

It has been sought to convert mononucleotides into neutral phosphotriesters capable of crossing the cell membrane and of intracellular delivery of the corresponding mononucleotide phosphotriester (NuMP). Such an approach has been adopted by various authors for a number of years, but has proved to be disappointing. The derivatives obtained were in general either excessively toxic or of insufficient extracellular stability, and did not in the end result provide any enhancement of the biological activity.

Thus, the use of phosphorylated nucleoside structures comprising bioreversible protecting groups of acyloxymethyl or acyloxybenzyl type has been proposed, for antitumor nucleoside derivatives such as 5-fluorouracil, in WO patents No. 9,008,155 and 9,119,721. However, these compounds are of limited chemical stability, and generate toxic formaldehyde metabolites in vivo. Furthermore, they are sparingly soluble and the yield of their chemical preparation is low.

The aim of the present invention is thus to provide other types of bioreversible groups which may be combined especially with mononucleotide or other structures such that the biological activity thereof is enhanced, in particular as regards compounds derived from or analogous to nucleosides having antiviral activity, and which reversible groups do not have the abovementioned drawbacks.

The present invention proposes to use novel groups, characterized by the presence of —S—S— and/or —S— / C=Z enzyme-labile bonds which lead, after enzymatic activation, to the formation of unstable intermediates that selectively release the corresponding monophosphate or monophosphonate.

More precisely, the subject of the present invention is the compound corresponding to the general formula I:

in which:

R is a radical —(CH$_2$)$_n$—S—X where:

X represents a radical

or —S—U,

Z being O or S,

Y and U representing an alkyl, aryl or saccharide radical which is optionally substituted, in particular with an OH, SH or NH group, and n is equal to 1 to 4, preferably 1 or 2, and Nu is a radical consisting of a residue of a biologically active compound or the dephosphorylated residue of a compound which is biologically active when it bears a phosphate or phosphonate group.

When, in the formula (I), Nu is linked to the phosphorus by a P—O bond, the compound of formula (I) according to the invention bears a phosphate group and thus constitutes a phosphotriester compound.

When Nu is linked to the phosphorus by a P—C bond, the compound of formula (I) according to the invention bears a phosphonate group.

The mechanisms of bioreversibility of the radicals R take place via enzymatic cleavage of the S—X bonds and release of the $(CH_2)_n$—S residues, according to a mechanism which is illustrated by the examples represented FIG. 1.

For Y and U there are especially mentioned, as alkyl group, a $C_1$ to $C_7$ alkyl; as aryl group, phenyl and benzyl radicals, and, as saccharide radicals, glucose, mannose or rhamnose.

In one embodiment, when X represents SU, U preferably represents the radical —$(CH_2)_{n^1}$—$X^1$ where $X_1$ represents H, OH, SH or $NH_2$ and $n^1$ is equal to 1 to 4, preferably 1 or 2.

There are especially mentioned the compounds (I) in which R represents —$(CH_2)_2$—S—S—$(CH_2)_2$—OH.

In another embodiment, when X represents

appropriately represents $CH_3$ or tBu.

There are especially mentioned the compounds (I) for which R represents

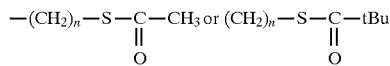

with n=1 or 2.

In an advantageous embodiment of the present invention, for the compounds (I), there are especially mentioned the compounds for which Nu represents a 5' residue of a natural nucleoside or of a derivative of a natural nucleoside, which is therapeutically active or for which the 5'-(O)-monophosphate or 5'-(C)-monophosphonate is therapeutically active.

These compounds of formula (I) generally have antiviral or antitumor activity.

The compounds of formula (I) for which Nu represents a 5' residue of 2',3'-dideoxynucleoside or 2',3'-didehydronucleoside are more particularly mentioned.

The compounds (I) for which Nu is a 5' residue of ddU (dideoxyuridine), ddT (dideoxythymidine), ddC (dideoxycytidine), AZT (3'-azido-2',3'-dideoxythymidine) and the derivatives thereof, especially those substituted on the pyrimidine base or at 2' and 3' of the saccharide ring, are more particularly mentioned among the compounds (I) derived from dideoxynucleosides having antiviral activity.

ddT, ddC or AZT are illustrations of the radicals Nu which represent a 5' residue of a therapeutically active natural nucleoside derivative.

ddU is an illustration of the radicals Nu which represent a 5' residue of a nucleoside derivative which is only active in phosphorylated form. ddU (dideoxyuridine) is not enzymatically monophosphorylated in vivo. Only the triphosphate thereof is a polymerase inhibitor and imparts antiviral activity thereto.

The compounds for which Nu represents a 5' residue of the derivatives 5-fluorouridine or 5-fluoro-2'-deoxyuridine or 1-β-D-arabinofuranosylcytosine are especially mentioned among the compounds (I) having antitumor activity. These compounds illustrate the advantage of the functionalization according to the invention in order to circumvent the resistance acquired to certain nucleoside drugs when this resistance is due to a loss of their ability to be monophosphorylated, as is often the case in antitumor chemotherapy.

According to another embodiment variant of the invention, in the compounds (I) the radical Nu represents a nucleoside analog residue such as a carbonucleoside (nucleoside in which the oxygen of the saccharide ring is replaced by a carbon), a phosphononucleoside (nucleoside in which the oxygen at 5' is replaced by a carbon) or a purine- or pyrimidine-based derivative of acyclonucleoside type, that is to say one which contains no saccharide ring, such as ACV (aciclovir), or a methoxyalkylpurine or pyrimidine radical of formula $CH_2$—O-alkylpurine or -pyrimidine.

The compounds (I) for which Nu represents a methoxyalkylpurine or -pyrimidine radical are illustrations of the phosphonate compounds. In the particular case of phosphonylmethoxyalkylpurine or -pyrimidine antiviral compounds, PMEA, HPMPA or HPMPC are especially mentioned, the formulae of which are given in FIGS. 3 and 4.

Thus, the present invention relates in particular to compounds in which Nu is a 3-hydroxy-2-methoxypropylpurine or -pyrimidine radical of formula: —$CH_2$—O—CH($CH_2OH$)—$CH_2$-purine or -pyrimidine or a 2-methoxyethylpurine or -pyrimidine radical of formula —$CH_2$—O—$C_2H_4$-purine or -pyrimidine and, for example, the compounds (I) for which Nu is a methoxyethyladenine or 3-hydroxy-2-methoxypropylcytosine radical.

When Nu represents a dephosphonylated residue (dephosphated or dephosphonated) of a molecule which is biologically active when it is in phospate or phosphonate form, the functionalization according to the invention may enable the physicochemical and biophysical parameters of the said molecule comprising a phosphate or phosphonate group to be modified in general. Compound (I) may then consist, for example, of a phosphopeptide or phospholipid compound.

When Nu represents a residue of a nucleoside, of a nucleoside derivative or of a nucleoside analog, the latter may be D or L enantiomers.

The compounds according to the invention may be prepared by processes known to those skilled in the art.

In particular, the subject of the present invention is a process for the preparation of the compounds according to the invention, characterized in that a compound of formula (I) is prepared, in which compound the functional groups of R, and possibly of Nu, are protected by suitable protecting groups, followed by deprotection of the said functional groups of R, and possibly of Nu, in order to obtain the compounds of formula (I).

In particular, a compound of formula (II):

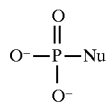

where Nu is possibly protected, is reacted in an appropriate manner with the compound of formula (III), X—S—(CH$_2$)$_n$—OH, where X is protected, in order to obtain the said protected compound of formula (I), which is then deprotected.

In a particular embodiment, the reaction between the compounds of formula (II) and (III) takes place in the presence of a condensing agent such as MSNT, in pyridine.

Other preparation processes are illustrated in the examples which follow, in which other characteristics and advantages of the present invention will also appear.

The description refers to FIGS. 1 to 6, in which:

FIG. 3 represents the formula of certain compounds according to the invention.

FIG. 4 represents a preparation scheme for compounds prepared in Example 1, and the formula of the compounds HPMPA and HPMPC.

FIG. 5 represents the preparation schemes for compounds prepared in Examples 2 and 3.

FIG. 6 represents the preparation scheme for compounds prepared in Example 4.

FIG. 7 represents the preparation scheme for compounds prepared in Examples 6–14.

Figure 1:
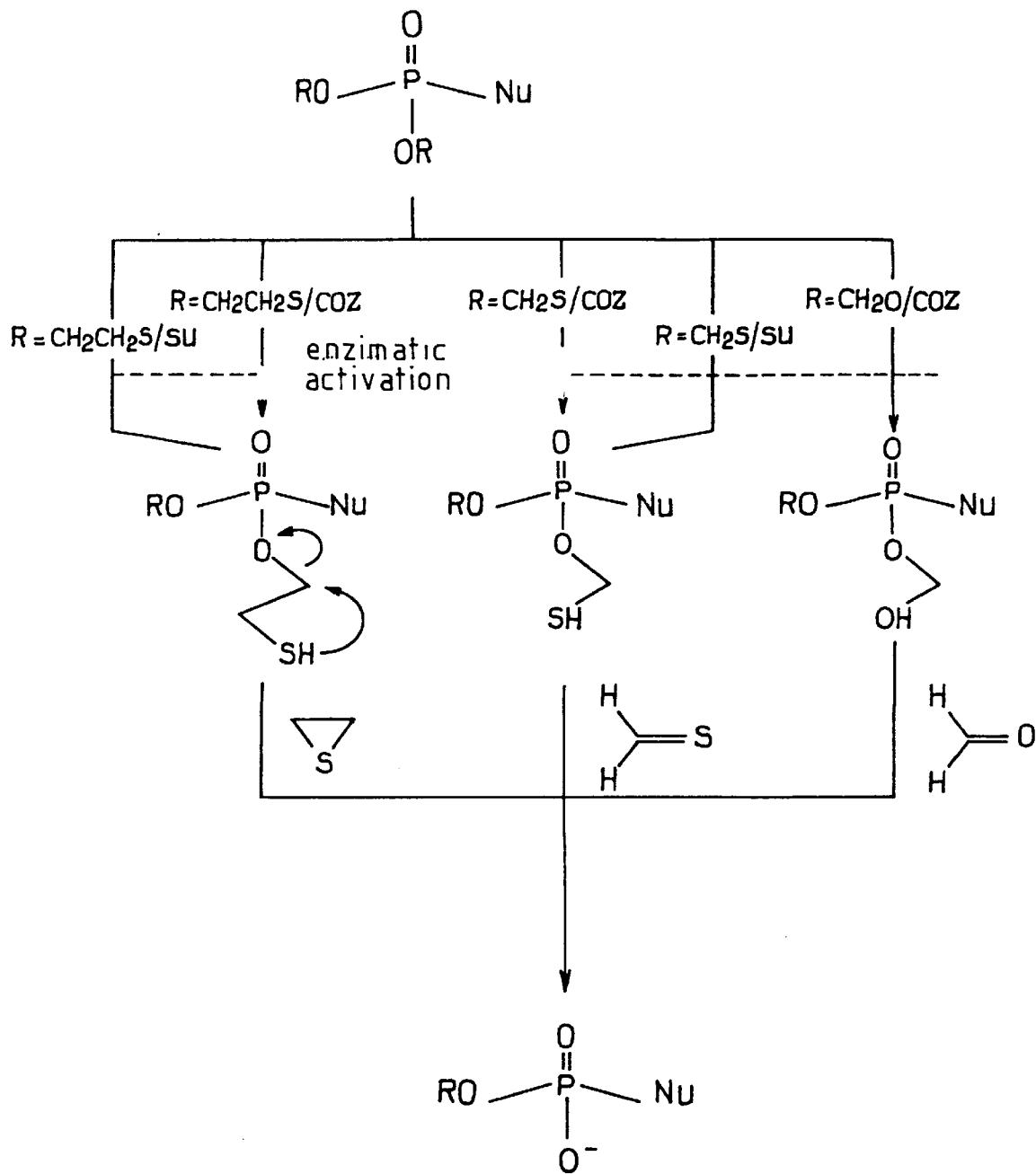
FIG. 1 represents decomposition mechanisms for groups which are bioreversible under enzymatic activation. The same mechanism takes place for both groups R.
Figure 2:
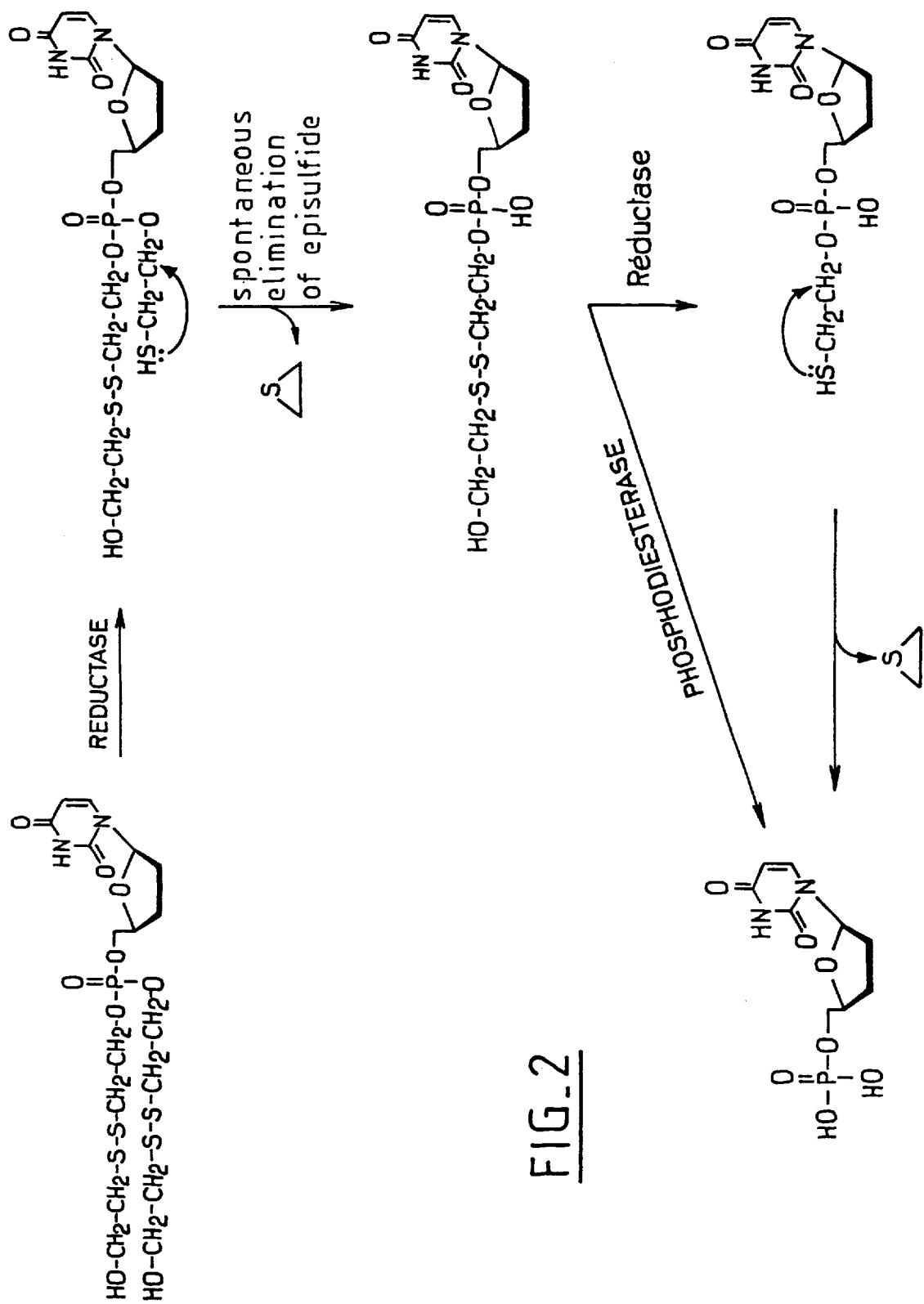
FIG. 2 represents the decomposition mechanism for the bioreversible group of the compound of Example 2.

The advantage of this invention resides in the difference in stability of the mononucleotide phosphotriesters between extracellular and intracellular media; it is initially shown that the decomposition of one of the compounds described in the invention (Example 2) complies fully with the above-mentioned criteria and occurs according to the mechanism shown FIG. 2.

The "ISRP on line" HPLC technique ("On-line Internal Surface Reversed-Phase Cleaning: The Direct HPLC Analysis of Crude Biological Samples", A. POMPON, I. LEFEBVRE and J. L. IMBACH, Biochemical Pharmacology, 43, 1769–1775 (1992) was used for this study, the compound studied being incubated respectively in culture medium (RPMI/10% inactivated serum) and in a total cell extract (CEM).

The compound of Example 2 has a half-life of 9 hours in culture medium and of less than 5 minutes in cell extract. The corresponding intracellular release of NuMP is corroborated by the demonstration of biological activity, whereas the constituent nucleoside is inactive.

Furthermore, insofar as the rate-determining step for activation of the phosphotriester into mononucleotide is highly dependent on the initial kinetics of enzyme hydrolysis, a variation in the nature of the enzyme-labile groups leads to a modulation of the pharmacokinetic parameters of the drug and results in delay-actions.

These data clearly confirm the advantage of the invention.

Thin layer chromatographies were performed on Merck 60F 254 silica plates (Art. 5554). Column chromatographies on silica gel were carried out with Merck 60 H silica (Art. 7736) or with RP2 Merck silanized silica (Art. 7719). Before analysis or lyophilization, the solutions were filtered on Millex HV-4 filter (Millipore).

The UV spectra were recorded on a UVIKON 810 spectrophotometer.

Mass spectra were taken on a JEOL JMS DX 300 apparatus by the FAB ionization method in positive or negative mode in a matrix of glycerol (G), glycerol/thioglycerol (GT) or 3-nitrobenzyl alcohol (NBA).

Proton NMR spectra were recorded on a Varian EM 360 apparatus or on a Brüker AC 250 apparatus. The chemical shifts are expressed in ppm relative to the tetramethylsilane (TMS) signal. The multiplicity and the appearance of the signals observed by NMR are indicated by one (or more) letter(s): s (singlet), d (doublet), t (triplet), m (multiplet), b (broad). Phosphorus NMR spectra were recorded on a Brüker WP 200 SY apparatus with proton decoupling. The chemical shifts are expressed in ppm relative to the H$_3$PO$_4$ signal which is taken as external reference.

EXAMPLE 1

O-(2',3'-dideoxyuridin-5'-yl)-O,O'-bis(S-acetyl-2-thioethyl)phosphate (1)

(Scheme in FIG. 4)

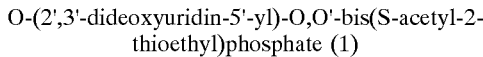

A solution of 1.0 ml (14 mmol) of thioacetic acid in 5 ml of toluene is treated with 0.90 ml (12 mmol) of iodoethanol in the presence of 1.7 ml (12 mmol) of 1,8-diazabicyclo-(5.4.0)-7-undecene (DBU) for 2 hours. The reaction medium is diluted with dichloromethane and washed with water. The organic phase is dried over sodium sulfate and evaporated. The crude product obtained is purified on a column of silica gel (eluent: methanol (0–4%) in dichloromethane) to give 1.2 g (85%) of 5 in the form of an oil.

5: $^1$H NMR (DMSO-d$_6$): d=2.32 (s, 3H, CH$_3$); 2.91 (t, 2H, CH$_2$S, J=6.6 Hz); 3.45 (pseudo q, 2H, CH$_2$OH, J=6 Hz); 4.97 (t, 1H, OH) ppm.

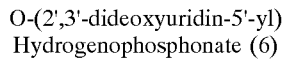

A 1.5M solution of phosphorous acid (165 ml, 247 mmol) in anhydrous pyridine is added to 5.25 g of 2',3'-dideoxyuridine (24.7 mmol) and is treated with 16.8 ml of pivaloyl chloride (136 mmol). After reaction for 3 hours, aqueous 1M triethylammonium bicarbonate solution is added to neutralize the mixture and the solvent is evaporated off under reduced pressure. The oil obtained is chromatographed on a column of silica gel (eluent: methanol (0–35%) in dichloromethane) to give 6. The product is taken up in methanol and is filtered on a Millipore filter. Evaporation of the solvent gives 7.10 g (76%) of 6 (in triethylammonium form) which is sufficiently pure for use in the next step of the synthesis. A sample of higher purity is obtained after an additional purification by thin layer chromatography on silica gel, using a mixture of isopropanol, ammonia solution and water (8:1:1) as eluent. The product, in ammonium form, is extracted from the silica with methanol, the solvent is stripped off by evaporation and the residue is taken up in water, filtered on a Millipore filter and lyophilized.

6: UV (H$_2$O): lmax=262 nm (e 9940); lmin=230 nm (e 2080)

MS (negative FAB, GT); 275 (M)$^-$. $^1$H NMR (DMSO-d$_6$); d=1.78–2.05 (m, 3H, H-2',3',3"); 2.18–2.45 (m, 1H, H-2"); 3.65–3.95 (m, 2H, H-5',5"); 4.11 (m, 1H, H-4'); 5.55 (d, 1H, H-5, J=8.1 Hz); 5.95 (dd, 1H, H-1', J=6.8 and 3.8 Hz); 6.63 (d, 1H, HP, J=592 Hz); 7.87 (d, 1H, H-6, J=8.1 Hz) ppm $^{31}$P NMR (DMSO-d$_6$): d=1.60 ppm.

O-(2',3'-dideoxyuridin-5'-yl)-O,O'-bis(S-acetyl-2-thioethyl)phosphate (1)

A solution of 200 mg (0.530 mmol) of the hydrogenophosphonate 6 of 2',3'-dideoxyuridine in 5 ml of pyridine is treated with 196 μl of pivaloyl chloride for 30 minutes. 159 mg (1.33 mmol) of 2-hydroxyethyl acetyl sulfide (5) are added and the reaction is left stirring for 2 hours. The phosphite formed is oxidized using 2% iodine solution in a pyridine-water mixture (98:2) until a persistent coloration is obtained (7–8 ml). The solvent is evaporated off under reduced pressure. The crude product obtained is co-evaporated with toluene and chromatographed on a column of silica gel (eluent: methanol (0–6%) in dichloromethane) to give 65 mg (25%) of compound 1 in the form of an oil.

1: UV (EtOH): lmax=262 nm (e 9400); lmin=230 nm (e 2500)
MS (positive FAB): 497 (M+H)$^+$. $^1$H NMR (DMSO-d$_6$): d=1.73–2.13 (m, 3H, H-2',3',3"); 2.20–2.4 (m, 1H, H-2"); 2.356 and 2.360 (s and s, 3H and 3H. 2 CH$_3$); 3.13 (t, 4H, 2 CH$_2$S, J=6.4 Hz); 4.00–4.26 (m, 7H, H-4', 5',5" and 2 CH$_2$CH$_2$OP); 5.60 (d, 1H, H-5, J=8.1 Hz); 6.01 (d, 1H, H-1', J=4.2 and 7.0 Hz); 7.64 (d, 1H, H-6, J=8.1 Hz); 11.3 (bs, 1H, NHCO) ppm. $^{31}$P NMR (DMSO-d$_6$): d=−1.21 ppm

EXAMPLE 2

O,O-Bis(S-(2-hydroxyethylsulfidyl)-2-thioethyl)-O-(2',3'-dideoxyuridin-5'-yl)phosphate (2)

(Scheme in FIG. 5)

O,O'-Bis(S-(O-(4-methoxytrityl)-2-oxethylsufidyl)-2-thioethyl)phosphate (8)

To a solution of 0.910 g (13.4 mmol) of imidazole in 18 ml of pyridine at 0° C. is added 0.406 ml (4.45 mmol) of phosphorus oxychloride. The mixture is stirred for 30 minutes at room temperature, then added to 3.80 g (8.91 mmol) of mono-O-(4-methoxytrityl)dithiodiethanol (7). After 18 hours, the reaction mixture is treated with 1M triethylammonium acetate solution. The reaction products are extracted with dichloromethane and the organic phase is washed with water, dried over sodium sulfate, concentrated under reduced pressure and co-evaporated with toluene. Purification on a column of silica gel (eluent: methanol (0–10%) in dichloromethane) gives 2.2 g (48%) of 8 in the form of the triethylammonium salt.

8: MS (negative FAB, NBA): 913 (M$^-$). $^1$H NMR (DMSO-d$_6$): 1.14 (t, 9H, (CH$_3$CH$_2$)$_3$NH$^+$, J=7.3 Hz); 2.78 (t, 4H, 2 SCH$_2$CH$_2$OP, J=6.4 Hz); 2.86 (t, 4H, 2 SCH$_2$CH$_2$OMTr, J=6 Hz); 2.99 (q, 6H, (CH$_3$CH$_2$)$_3$NH$^+$, J=7.3 Hz); 3.21 (t, 4H, 2 CH$_2$OMTr, J=5.9 Hz); 3.71 (s, 6H, 2 CH$_3$O); 3.87 (m, 4H, 2 CH$_2$OP); 6.82–7.45 (m, 28H, 2 Tr) ppm. $^{31}$P NMR (DMSO-d$_6$): −2.70 ppm.

O,O'-Bis(S-(2-hydroxyethylsufidyl)-2-thioethyl)-O-(2',3'-dideoxyuridin-5'-yl)phosphate (2)

A mixture of 666 mg (0.655 mmol) of 8 and 139 mg (0.656 mmol) of 2',3'-dideoxyuridine in 5 ml of pyridine is treated with 486 mg (1.64 mmol) of 1-(2-mesitylenesulfonyl)-3-nitro-1,2,4-triazole. After 30 hours, the reaction mixture is diluted with dichloromethane and washed with aqueous 1M triethylammonium acetate solution and then with water. The organic phase is dried over sodium sulfate, concentrated under reduced pressure, co-evaporated with toluene and chromatographed on a column of silica gel (eluent: methanol (0–4%) in dichloromethane). The partially purified protected phosphotriester is treated with 5 ml of the acetic acid/water/methanol mixture (8:1:1) for 24 hours. The solvents are stripped off by evaporation under reduced pressure and the oil obtained is co-evaporated with toluene. Purification on a column of silica gel (eluent: methanol (0–6%) in dichloromethane) followed by purification on a column of silanized silica (eluent: ethanol (0–40%) in water) gives 52 mg (14%) of compound 2 after lyophilization in dioxane.

2: UV (EtOH): λ max 261 nm (ε 9900). λ min 231 nm (ε 3100). MS (positive FAB, GT): 565 (M+H)$^+$: 489 (M−SCH$_2$CH$_2$OH+2H)$^+$; 429 (M−HOCH$_2$CH$_2$SSCH$_2$CH$_2$+2H)$^+$. $^1$H NMR (DMSO-d$_6$): 1.63–1.9 (m, 1H, H-3'); 1.9–2.10 (m, 2H, H-2'3"); 2.33–2.40 (m, 1H, H-2"); 2.80 (t, 2H, HOCH$_2$CH$_2$S, J=6.4 Hz); 2.81 (t, 2H, HOCH$_2$CH$_2$S, J=6.4 Hz); 3.00 (t, 4H, 2 SCH$_2$CH$_2$OP, J=6.3 Hz); 3.61 (pseudo q, 4H, 2, HOCH$_2$, J=6 Hz); 4.07–4.32 (m, 7H, H-4',5',5" and 2 CH$_2$CH$_2$OP); 4.89 (t, 2H, 2 HO, J=4.9 Hz); 5.598 (d, 1H, H-5, J=8.1 Hz); 5.604 (d, 1H, H-5, J=8.1 Hz); 6.00 (dd, 2H, 2H-1', J=4.1 and 7.9 Hz); 7.65 (d, 2H, 2 H-6, J=8.0 Hz); 11.31 (bs, 1 H, NHCO) ppm. $^{31}$P NMR (DMSO-d$_6$): −0.880 ppm

EXAMPLE 3

O,O'-Bis(S-(2-hydroxyethylsufidyl)-2-thioethyl)-O-(3'-azido-3'-deoxythymidin-5'-yl)phosphate (3)

(Scheme in FIG. 5)

A mixture of 666 mg (0.655 mmol) of 8 and 193 mg (0.722 mmol) of 3'-azido-3'-deoxythymidine in 5 ml of pyridine is treated with 486 mg (1.64 mmol) of 1-(2-mesitylenesulfonyl)-3-nitro-1,2,4-triazole. After 24 hours, 194 mg (0.656 mmol) of 1-(2-mesitylenesulfonyl)-3-nitro-1,2,4-triazole are added and the reaction is left for a further 24 hours. The reaction mixture is then diluted with dichloromethane and washed with aqueous 1M triethylammonium acetate solution and then with water. The organic phase is dried over sodium sulfate, concentrated under reduced pressure, co-evaporated with toluene and chromatographed on a column of silica gel (eluent: methanol (0–2%) in dichloromethane). The partially purified protected phosphotriester is treated with 5 ml of the acetic acid/water/methanol mixture (8:1:1) for 24 hours. The solvents are stripped off by evaporation under reduced pressure and the oil obtained is co-evaporated with toluene. Purification on a column of silica gel (eluent: methanol (0–6%) in dichloromethane) gives 130 mg (29%) of compound 3 after lyophilization in dioxane.

3: UV (EtOH): λ max 264 nm (ε 9600). λ min 234 nm (ε 2100). MS (positive FAB, GT): 620 (M+H)$^+$; 544 (M-SCH$_2$CH$_2$OH+2H)$^+$. $^1$H NMR (DMSO-d$_6$): 1.80 (s, 3H, CH$_3$); 2.26–2.5 (m, 2H, H-2',2"); 2.796 (t, 2H, HOCH$_2$CH$_2$S, J=6.4 Hz); 2.802 (t, 2H, HOCH$_2$CH$_2$S, J=6.4 Hz); 2.99 (t, 4H, 2 SCH$_2$CH$_2$OP, J=6.3 Hz); 3.61 (pseudo q, 4H, 2 HOCH$_2$, J=6 Hz); 4.02 (m, 1H, H-4'); 4.09–4.44 (m, 6H, H-5',5" and 2 CH$_2$CH$_2$OP); 4.48 (m, 1H, H-3'); 4.90 (t, 2H, 2 HO, J=5.3 Hz); 6.14 (t, 1H, H-1', J=6.6 Hz); 7.49 (s, 1H, H-6); 11.37 (bs, 1H, NHCO) ppm. $^{31}$P NMR (DMSO-d$_6$): −0.954 ppm

EXAMPLE 4

9-(2-(O,O'-Bis(S-(2-hydroxyethylsufidyl)-2-thioethyl)phosphonylmethoxy-ethyl)adenine (4)

(Scheme in FIG. 5)

N$^6$-(4-Methoxytrityl)-9-(2-diethoxyphosphonylmethoxyethyl)adenine (10)

A solution of 3.93 g (11.9 mmol) of 9-(diethoxyphosphonylmethoxyethyl)adenine (9) (A. Holy et al., *Collection Czechoslovak Chem. Commun.* 52 2792, 1987) and 146 mg (1.19 mmol) of 4-dimethylaminopyridine in 50 ml of dichloromethane is treated with 3.31 ml (23.8 mmol) of triethylamine and 7.35 g (23.8 mmol) of 4-methoxytrityl chloride for 4 hours. The reaction mixture is then diluted with dichloromethane and washed with aqueous sodium hydrogen carbonate solution and then with water. The organic phase is dried over sodium sulfate and concentrated under reduced pressure. Chromatography on a column of silica gel (eluent: methanol (0–3%) in dichloromethane) allows 5.43 g (84%) of compound 10 to be isolated.

10: UV (EtOH): $\lambda$ max 275 nm ($\epsilon$ 27200). $\lambda$ min 246 nm ($\epsilon$ 11200) MS (negative FAB, GT): 601 (M–H)$^-$; 406 (A$^{MTr}$)$^-$; 328 (M-MTr)$^-$. $^1$H NMR (DMSO-d$_6$): 1.10 (t, 6H, 2 C$\underline{H}_3$CH$_2$, J=7.0 Hz); 3.71 (s, 3H, CH$_3$O), 3.80–3.98 (m, 4H, PC$\underline{H}_2$ and C$\underline{H}_2$CH$_2$); 3.88 (q, 4H, 2 CH$_3$C$\underline{H}_2$, J=8 Hz); 4.33 (t, CH$_2$C$\underline{H}_2$, J=4.8 Hz); 6.80–7.37 (m, 14H, Tr); 7.91 (s, 1H, H-8); 8.18 (s, H-2) ppm. $^{31}$P NMR (DMSO-d$_6$): 21.35 ppm.

N$^6$-(4-Methoxytrityl)-9-(2-phosphonylmethoxyethyl) adenine (11)

A solution of 5.00 g (8.31 mmol) of 10 in 29 ml of acetonitrile is treated with 3.29 ml (24.9 mmol) of trimethylsilyl bromide for 14 hours. The excess reagent and the solvent are stripped off by evaporation under reduced pressure. The oil obtained is taken up in triethylammonium bicarbonate and concentrated under reduced pressure. Purification is performed by chromatography on a column of silica gel (eluent: methanol (0–50%) in dichloromethane). After filtration in solution in dichloromethane, 3.4 g (63%) of 11 are isolated in the form of a mixed salt of acid and triethylammonium (1:1).

11: MS (negative FAB, GT): 544 (M–H)$^-$; 272 (M-MTr)$^-$. $^1$H NMR (DMSO-d$_6$): 1.11 (t, 9H, (C$\underline{H}_3$CH$_2$)NH$^+$, J=7.3 Hz); 2.96 (q, 6H, (C$\underline{H}_3$CH$_2$)NH$^+$, J=7.3 Hz); 3.34 (d, 2H, PCH$_2$, J=8.4 Hz); 3.68 (s, 3H, CH$_3$O); 3.8 (m, 2H, C$\underline{H}_2$CH$_2$); 4.27 (t, CH$_2$C$\underline{H}_2$, J=4.5 Hz); 6.65–7.35 (m, 14H, Tr); 7.83 (s, 1H, H-8); 8.31 (s, 1H, H-2) ppm. $^{31}$P NMR (DMSO-d$_6$): 11.40 ppm.

N$^6$-(4-Methoxytrityl)-9-(2-(O,O'-bis (S-(O-(4-methoxytrityl)-2 -oxethylsufidyl)-2-thioethyl)) phosphonylmethoxyethyl)adenine (12).

A mixture of 296 mg (0.458 mmol) of 11 with 977 mg (2.29 mmol) of mono-O-(4-methoxytrityl)dithiodiethanol (7) in 5 ml of pyridine is treated with 341 mg (1.15 mmol) of 1-(2-mesitylenesulfonyl)-3-nitro-1,2,4-triazole. After 3 days, the reaction mixture is diluted with dichloromethane and washed with saturated aqueous sodium hydrogen carbonate solution and then with water. The organic phase is dried over sodium sulfate, concentrated under reduced pressure, co-evaporated with toluene and chromatographed on a column of silica gel (eluent: methanol (0–5%) in dichloromethane) to give 330 mg (53%) of 12.

12: UV (EtOH): $\lambda$ max 275 nm ($\epsilon$ 28200). $\lambda$ min 253 nm ($\epsilon$ 18300). MS (negative FAB, NBA): 1360 (M–H)$^-$; 952 (M-MTrOCH$_2$CH$_2$SSCH$_2$CH$_2$)$^-$. $^1$H NMR (DMSO-d$_6$): 2.75 (t, 4H, 2 SC$\underline{H}_2$CH$_2$OP, J=6.3 Hz), 2.86 (t, 4H, 2 SC$\underline{H}_2$CH$_2$OMTr, J=5.9 Hz); 3.19 (t, 4H, 2 C$\underline{H}_2$OMTr, J=6.0 Hz); 3.68 (s, 3H, CH$_3$O); 3.69 (s, 6H, 2 CH$_3$O); 3.83 (m, 4H, PCH$_2$ and C$\underline{H}_2$CH$_2$); 4.05 (m, 4H, 2 C$\underline{H}_2$OP); 4.28 (t, 2H, CH$_2$C$\underline{H}_2$, J=4.6 Hz); 6.87–7.45 (m, 42H, 3 Tr); 7.88 (s, 1H, H-8); 8.12 (s, 1H, H-2)ppm. $^{31}$P NMR (DMSO-d$_6$): 22.09 ppm.

9-(2-(O,O'-Bis(S-(2-hydroxyethylsufidyl)-2-thioethyl)phosphonylmethoxyethyl)adenine (4)

The phosphotriester 12 (290 mg, 0.213 mmol) is treated with 15 ml of the acetic acid/water/methanol mixture (8:1:1) for 15 hours. The solvents are stripped off by evaporation under reduced pressure and the oil obtained is co-evaporated with toluene. Purification on a column of silica gel (eluent: methanol (0–8%) in dichloromethane) gives 116 mg (90%) of compound 4 after lyophilization in the water/dioxane mixture.

4: UV (EtOH): $\lambda$ max 260 nm ($\epsilon$ 14700). $\lambda$ min 228 nm ($\epsilon$ 3600). MS (positive FAB, GT): 545 (M+H)$^+$. $^1$H NMR (DMSO-d$_6$): 2.80 (t, 4H, 2 SC$\underline{H}_2$CH$_2$OP, J=6.4 Hz); 2.91 (t, 4H, 2 SC$\underline{H}_2$CH$_2$OH, J=6.4 Hz); 3.61 (pseudo q, 4H, 2 C$\underline{H}_2$OH, J=6 Hz); 3.91 (t, 2H, C$\underline{H}_2$CH$_2$, J=5.1 Hz); 3.95 (d, 2H, PCH$_2$, J=8.2 Hz); 4.15 (m, 4H, 2 C$\underline{H}_2$OP); 4.32 (t, 2H, CH$_2$C$\underline{H}_2$, J=5.0 Hz); 7.20 (bs, 2H, NH$_2$); 8.08 (s, 1H, H-8); 8.14 (s, 1H, H-2) ppm. $^{31}$P NMR (DMSO-d$_6$): 22.24 ppm.

EXAMPLE 5

Evaluation of the Anti-HIV 1 Activity on CEM cells and MT-4 Cells

HIV=Human immunodeficiency virus
MT-4=Human leukemia T cell
CEM=Human lymphoblastoid T cell HIV-1 replication (LAI isolate) in CEM cells is measured by assaying the reverse transcriptase (RTase) in the culture supernatant after infection for 5 days. This activity reflects the presence of the virus released by the cells. After adsorption of the virus, the test compounds are added, at various concentrations, to the culture medium.

Antiviral activity is expressed as the lowest concentration of compound which reduces the production of RTase by at least 50% (ED$_{50}$).

The toxic effect on non-infected CEMs is assessed by a colorimetric reaction based on the capacity of living cells to reduce 3-(4,5-dimethylthiazol-2-yl)-2,5-diphenyltetrazolium bromide into formazan after incubation for 5 days in the presence of various concentrations of the compounds. The results are expressed as the lowest concentration of compound which results in at least 50% inhibition of the formation of formazan (CD$_{50}$).

The compounds used as examples in this invention have the following anti-HIV activities:

| Compound 1: | | | |
|---|---|---|---|
| ED$_{50}$ | CEM-TK$^-$, | $4 \cdot 10^{-6}$ M | (CD$_{50}$ $7 \cdot 10^{-5}$ M) |
| | CEM-SS, | $5 \cdot 10^{-6}$ M | (CD$_{50}$ $9 \cdot 10^{-5}$ M) |
| | MT4, | $2 \cdot 10^{-6}$ | (CD$_{50}$ $9 \cdot 10^{-5}$ M) |
| Compound 2: | | | |
| ED$_{50}$ | CEM-TK$^-$, | $8 \cdot 10^{-6}$ M | (CD$_{50}$ $8 \cdot 10^{-5}$ M) |
| | CEM-SS, | $6 \cdot 10^{-5}$ M | (CD$_{50}$ $10^{-4}$ M) |
| Compound 3: | | | |
| ED$_{50}$ | CEM-TK$^-$, | $7 \cdot 10^{-6}$ M | (CD$_{50}$ $8 \cdot 10^{-5}$ M) |
| | CEM-SS, | $7 \cdot 10^{-10}$ M | (CD$_{50}$ $8 \cdot 10^{-5}$ M) |
| | MT4, | $10^{-9}$ M | (CD$_{50}$ $8 \cdot 10^{-5}$ M) |
| Compound 4: | | | |
| ED$_{50}$ | CEM-TK$^-$, | $8 \cdot 10^{-8}$ M | (CD$_{50}$: $4 \cdot 10^{-5}$ M) |
| | CEM-SS, | $3 \cdot 10^{-6}$ M | (CD$_{50}$ > $10^{-4}$ M) |
| | MT4, | $8 \cdot 10^{-7}$ M | (CC$_{50}$: $2 \cdot 10^{-5}$ M) |

This set of data shows that there has indeed been intracellular release of the nucleoside monophosphate.

EXAMPLE 6

O,O'-Bis(S-acetyl-2-thioethyl)-N,N-diisopropylphosphoramidite

To a stirred solution of N,N-diisopropylphosphorodichloridate (4.04 g, 20 mmol) in tetrahydrofuran (150 ml) at -78° C. was added dropwise over 45 minutes a solution of S-acetylthioethanol (4.81 g, 40 mmol) and triethylamine (5.53, 40 mmol) in tetrahydrofuran (100 ml). The resulting reaction mixture was stirred for 2 hours at ambient temperature then filtered. The filtrate was concentrated under vacuum and the residue was diluted with cyclohexane and filtered. The filtrate was concentrated to a residue under vacuum, Diluted with cyclohexane, filtered and concentrate again. The final residue was chromatographed on a silica gel column. The column was eluted with a gradient of ethyl acetate in cyclohexane (0→20%) containing 5% triethylamine to obtain the title compound, O,O'-bis(S-acetyl-2-thioethyl-N,N-diisopropylphosphoramidite (5.3 g, 72%) . Mass Spec (FAB positive, GT): 370 (M+H)$^+$, 103 [$CH_3C(O)SCH_2CH_2$]$^+$. NMR $^1$H (DMSO-d$_6$): 3.70–3.47 (m, 6H, 2 C$\underline{H}_2$OP, 2 C$\underline{H}(CH_3)_2$); 3.04 (t, 4H, 2SC$\underline{H}_2$CH$_2$, J=6.4 Hz); 2.32 (s, 6H, 2C$\underline{H}_3$COS); 1.10 (d, 12H, 2 CH(C$\underline{H}_3$)$_2$), J=6.8 Hz) ppm. NMR $^{31}$P (DMSO-d$_6$): 147.9 ppm(q).

EXAMPLE 7

General Procedure for O-(2',3'-dideoxynucleosid-5'-yl)-O'-O"-bis(S-acetyl-2-thioethyl)phosphates To a solution of a 2',3'-dideoxynucleoside [AZT (0.1 g, 0.37 mmol); ddA (0.05 g, 0.5 mmol); ddI (0.12 g, 0.5 mmol); or ddT (0.11 g, 0.5 mmol)] and O,O'-bis(S-acetyl-2-thioethyl)-N,N'-diisopropylphosphoramidite (1.2 eq.) in a mixture of tetrahydofuran/dimethylforamide (1:1, v/v, 5 ml per mmol) was added sublimed tetrazole (3.0 eq). After 30 min of stirring at ambient temperature the reaction mixture was cooled to -40° C. and a suspension of 3-chloroperbenzoic acid (1.3 eq) in dichloromethane (2 ml per mmol) was added. After stirring for one hour at ambient temperature the excess peracid was reduced with an aqueous solution of 10% sodium thiosulfate. The crude residue was diluted with dichloromethane and extracted with a saturated aqueous solution of sodium bicarbonate. The organic phase was wash with water, dried over sodium sulfate, filtered and evaporated under vacuum. The residue was chromatographed on a silica gel column eluted with a step gradient of methanol in dichloromethane to give the title bis(SATE) phosphotriesters as pure products.

EXAMPLE 8

O-(2',3'-Dideoxy-3'-azidothymidin-5'-yl)-O,O'-bis(S-acetyl-2-thioethyl)phosphate [Bis(SATE)AZTMP]

Prepared as per the above general procedure to give 0.11 g (53%) of the title compound. UV (EtOH) $\lambda_{max}$ 264 nm ($\epsilon$ 9800), $\lambda_{min}$ 246 nm ($\epsilon$ 6500). Mass Spec. (FAB positive, GT): 552 (M+H)$^+$, (FAB negative, GT): 550(M−H)$^-$. NMR $^1$H (DMSO-d6): 11.36 (sl, 1H, NH-3) ; 7.46 (d, 1H, H-6, J$_{H-6, CH3-5}$=0.7 Hz); 6.13 (t, 1H, H-1', J$_{H1',2"}$=6.7 Hz) 4.46 (m, 1H, H-3'); 4.20 (m, 2H, H-5',5"); 4.03 (m, 5H, H-4', CH$_2$—C$\underline{H}_2$—O); 3.12 (t, 4H, S—C—$\underline{H}_{2a}$—CH$_{2b}$, J$_{Ha,Hb}$=6.3 Hz); 2.42 (m, 8H, H-2',2", C$\underline{H}_3$—CO); 1.78 (s, 3H, CH$_3$-5) ppm.

EXAMPLE 9

O-(2',3'-Dideoxyadenosin-5'-yl)-O,O'-bis(S-acetyl-2-thioethyl)phosphate [Bis(SATE)ddAMP]

Prepared as per the above general procedure to give 0.65 g (50%) of the title compound. UV (EtOH) $\lambda_{max}$ 260 nm ($\epsilon$ 12000), 229 nm ($\epsilon$ 8600), $\lambda_{min}$ 240 nm ($\epsilon$ 7200), 223 nm ($\epsilon$ 7900). Mass Spec. (FAB positive, GT): 520 (M+H)$^+$, 136 (BH$_2$)$^+$; (FAB negative, GT): 416 (M—CH$_3$C(O)SCH$_2$CH$_2$)$^-$, 134 (B)$^-$. NMR $^1$H (DMSO-d6): 8.25 & 8.13 (2s, 1H & 1H, H-2 & H-8); 7.24 (s, 2H, NH$_2$); 6.24 (t, 1H, J=5.4 Hz, H-1'); 4.28 (m, 1H, H-4'); 4.18–4.03 (m, 2H, H-5' & H-5"); 3.96 (q, 4H, 2 S—CH$_2$—C$\underline{H}_2$—O); 3.06 (t, 4H, J=6.3 Hz, 2 S—C$\underline{H}_2$—CH$_2$—O); 2.48 (m, 2H, H-2' & H-2"); 2.32 & 2.31 (2s, 3H & 3H, 2 CH$_3$) ppm. NMR $^{31}$P (DMSO-d$_6$) 0.78 ppm.

EXAMPLE 10

O-(2',3'-Dideoxyinosin-5'-yl)-O,O'-bis(S-acetyl-2-thioethyl)phosphate [Bis(SATE)ddIMP]

Prepared as per the above general procedure to give 0.21 g (81%) of the title compound. UV (EtOH) $\lambda_{max}$ 242 nm ($\epsilon$ 14700), 235 nm ($\epsilon$ 14900), shoulder 266 nm ($\epsilon$ 5800) & 248 nm ($\epsilon$ 13400). Mass Spec. (FAB positive, GT): 521 (M+H)$^+$, 137 (BH$_2$)$^+$, 103 (CH$_3$C(O)SCH$_2$CH$_2$)$^+$; (FAB negative, GT): 519 (M−H)$^-$, 135 (B)$^-$. NMR $^1$H (DMSO-d6): 12.36 (s, 1H, NH-1); 8.21 (s, 1H, H-2); 8.04 (s, 1H, H-8); 6.22 (m, 1H, H-1'); 4.28 (m, 1H, H-4'); 4.20–4.02 (m, 2H, H-5' & H-5"); 3.97 (m, 4H, 2 S—CH$_2$—C$\underline{H}_2$-OP); 3.07 (t, 4H, J=6.4 Hz, 2 S—C$\underline{H}_2$—CH$_2$); 2.49–2.42 (m, 2H, H-2' & H-2"); 2.33 (s, 3H, CH$_3$COS), 2.32 (s, 3H, CH$_3$COS), 2.15–2.02 (m, 2H, H-3' & H-3") ppm. NMR $^{31}$P (DMSO-d$_6$) 0.77 (m) ppm.

EXAMPLE 11

O-(2',3'-Dideoxythymidin-5'-yl)-O,O'-bis(S-acetyl-2-thioethyl)phosphate [Bis(SATE)ddTMP]

Prepared as per the above general procedure to give 0.23 g (91%) of the title compound. UV (EtOH) $\lambda_{max}$ 266 nm ($\epsilon$ 8800), $\lambda_{min}$ 246 nm ($\epsilon$ 5400). NMR $^1$H (DMSO-d6): 11.29 (s, 1H, NH-3); 7.47 (d, 1H, H-6; J=1.0 Hz); 6.01 (m, 1H, H-1'), 4.20–4.11 (m, 3H, H-4',H-5',5"); 4.04 (m, 4H, 2 CH$_2$—C$\underline{H}_2$-OP); 3.11 (t, 4H, S—C—$\underline{H}_{2a}$—CH$_{2b}$, J=6.3 Hz); 2.34 (s, 3H, C$\underline{H}_3$-COS); 2.33 (s, 3H, C$\underline{H}_3$-COS); 2.33–2.25 (m, 1H, H-2"); 2.00–1.90 (m, 3H, H-2",3',3"); 1.78 (d, 3H, CH$_3$-5, J=0.6 Hz) ppm. NMR $^{31}$p (DMSO-d$_6$) 0.56 ppm.

EXAMPLE 12

N$^6$-(4-Methoxytrityl)-9-(2-(O,O'-bis(S-acetyl-2-thioethyl)phosphonylmethoxyethyl)adenine [Bis(SATE)PMEA-MTr]

To a solution of N$^6$-(4-methoxytrityl)-9-(2-phosphonylmethoxyethyl)adenine (compound 11) as a mixture of triethylammonium salts (0.25:0.75, 0.3 g, 0.43 mmol), 1-(2-mesitylenesulfonyl)-3-nitro-1,2,4-triazole (0.41 g, 1.38 mmol) in anhydrous pyridine (6 ml) was added S-acetylthioethanol (0.33 g, 2.77 mmol). The reaction mixture was stirred overnight at ambient temperature and then neutralized with an aqueous triethylammonium bicarbonate (1M, pH 7.5, 4 ml). Chloroform and water were added, the organic phase was decanted, dried over sodium sulfate, filtered and evaporated under vacuum. The residue was chromatographed on a silica gel column eluted with a gradient methanol in dichloromethane (0→2%) to give the title compound, bis(SATE)PMEA-MTr (0.15 g, 50%), as an oil. Mass Spec. (FAB positive, GT): 750 (M+H)$^+$. NMR $^1$H (DMSO-d6): 8.15 & 7.90 (2s, 1H & 1H, H-2 & H-8); 7.31–6.81 (m, 15H, trityl & NH); 4.32 (t, 2H, J=4.7 Hz, CH$_2$N); 3.99–3.84 (m, 8H, 2 S—CH$_2$—C$\underline{H}_2$—O, CH$_2$—P, C$\underline{H}_2$—CH$_2$—N); 3.70 (s, 3H, OCH$_3$); 3.01 (t, 4H, J=6.4 Hz, S—C$\underline{H}_2$—CH$_2$—O); 2.30 (s, 6H, 2 CH$_3$) ppm. NMR $^{31}$P (DMSO-d$_6$) 22.51 ppm.

EXAMPLE 13

9-(2-(O,O'-Bis(S-acetyl-2-thioethyl) phosphonylmethoxyethyl)adenine [Bis(SATE) PMEA]

A solution of bis(SATE)PMEA$^{MTr}$ (0.21 g, 0.28 mmol) in acetic acid:water:methanol (8:1:1, v/v/v, 22 ml) was stirred overnight at ambient temperature. The reaction mixture was evaporated and the residue co-evaporated with 100% ethanol and dichloromethane. The residue was chromatographed on a silica gel column to give pure bis(SATE)PMEA (0.079 g, 59%). m.p. 66° C. (crystallized from toluene). UV (EtOH) $\lambda_{max}$ 260 nm ($\epsilon$ 14200), 230 nm ($\epsilon$ 10400), $\lambda_{min}$ 240 nm ($\epsilon$ 9200), 223 nm ($\epsilon$ 9800). Mass Spec. (FAB positive, GT): 570 (M+G+H)$^+$, 478 (M+H)$^+$; (FAB negative, GT): 374 (M—CH$_3$C(O)SCH$_2$CH$_2$)$^-$. NMR $^1$H (DMSO-d6): 8.12 & 8.06 (2s, 1H & 1H, H-2 & H-8); 7.17 (s, 2H, NH$_2$); 4.31 (t, 2H, J=5.0 Hz, CH$_2$N); 4.00–3.86 (m, 8H, 2 S—CH$_2$—C$\underline{H}_2$—O, CH$_2$—P, C$\underline{H}_2$—CH$_2$—N); 3.03 (t, 4H, J=6.4 Hz, 2 S—C$\underline{H}_2$—CH$_2$—O); 2.33 (s, 6H, 2 CH$_3$) ppm. NMR $^{31}$P (DMSO-d$_6$) 22.53 ppm.

EXAMPLE 14

Evaluation of the Anti-HIV 1 Activity on CEM Cells and MT-4 Cells of Bis(SATE)Phosphotriesters of AZT, ddA, ddI, ddT and PMEA The compounds were tested as described in Example 5 above.

| | | | |
|---|---|---|---|
| -AZT | | | |
| ED$_{50}$ | CEM-TK$^-$ | >10$^{-4}$ M | (CD$_{50}$ > 10$^{-4}$ M) |
| | CEM-SS | 4.8 10$^{-9}$ M ± 2.4 10$^{-9}$ | (CD$_{50}$ > 10$^{-4}$ M) |
| | MT-4 | 1.8 10$^{-8}$ M ± 0.6 10$^{-8}$ | (CD$_{50}$ > 10$^{-4}$ M) |
| -Bis(SATE)AZTMP | | | |
| ED$_{50}$ | CEM-TK$^-$ | 3.9 10$^{-8}$ M | (CD$_{50}$ ND) |
| | CEM-SS | 2.2 10$^{-8}$ M | (CD$_{50}$ ND) |
| | MT-4 | 7.8 10$^{-8}$ M | (CD$_{50}$ 7.6 10$^{-5}$ M) |
| -ddA | | | |
| ED$_{50}$ | CEM-TK$^-$ | 1.1 10$^{-6}$ M | (CD$_{50}$ > 10$^{-4}$ M) |
| | CEM-SS | 5.4 10$^{-7}$ M ± 1.1 10$^{-7}$ | (CD$_{50}$ > 10$^{-4}$ M |
| | MT-4 | 10$^{-5}$ M | (CD$_{50}$ > 10$^{-4}$ M) |
| -Bis(SATE) ddAMP | | | |
| ED$_{50}$ | CEM-TK$^-$ | 7.7 10$^{-10}$ M | (CD$_{50}$ > 10$^{-5}$ M) |
| | CEM-SS | 5.6 10$^{-10}$ M ± 3.4 10$^{-10}$ | (CD$_{50}$ 2.4 10$^{-5}$ M) ± 0.1 10$^{-5}$ |
| | MT-4 | 1.1 10$^{-8}$ M ± 0.8 10$^{-8}$ | (CD$_{50}$ 1.6 10$^{-5}$ M) ± 0.9 10$^{-5}$ |
| =ddI | | | |
| ED$_{50}$ | CEM-TK$^-$ | 9.5 10$^{-7}$ M | (CD$_{50}$ > 10$^{-4}$ M) |
| | CEM-SS | 4.3 10$^{-6}$ M ± 2.0 10$^{-6}$ | (CD$_{50}$ > 10$^{-4}$ M) |
| | MT-4 | 1.1 10$^{-5}$ M ± 0.2 10$^{-5}$ | (CD$_{50}$ > 10$^{-4}$ M) |
| -Bis(SATE) ddIMP | | | |
| ED$_{50}$ | CEM-TK- | 3.0 10$^{-7}$ M | (CD$_{50}$ > 10$^{-4}$ M) |
| | CEM-SS | 1.2 10$^{-6}$ M ± 0.6 10$^{-6}$ | (CD$_{50}$ > 10$^{-4}$ M |
| | MT-4 | 3.4 10$^{-6}$ M ± 1.1 10$^{-6}$ | (CD$_{50}$ > 10$^{-4}$ M |
| -ddT | | | |
| ED$_{50}$ | CEM-TK$^-$ | >10$^{-4}$ M | (CD$_{50}$ > 10$^{-4}$ M) |
| | CEM-SS | 4.0 10$^{-6}$ M | (CD$_{50}$ > 10$^{-4}$ M) |
| | MT-4 | ND | (CD$_{50}$ ND) |
| -Bis(SATE)ddTMP | | | |
| ED$_{50}$ | CEM-TK$^-$ | 5 10$^{-7}$ M | (CD$_{50}$ > 10$^{-4}$ M) |
| | CEM-SS | 1.7 10$^{-6}$ M | (CD$_{50}$ 8.5 10$^{-5}$ M) |
| | MT-4 | ND | (CD$_{50}$ ND) |

In the same manner as was seen for the activities exhibited in Example 5, the anti HIV activity of the above listed bis(SATE) derivatives show increases of up to 1/3 log units compared to their parent nucleosides (compare AZTMP and ddTMP to the parent nucleosides AZT and ddT, respectively). This increase in activity shows that there was intercellular release of the nucleoside monophosphate.

We claim:

1. A compound having the formula:

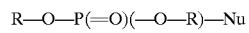

R—O—P(=O)(—O—R)—Nu wherein:
each R is, independently, —(CH$_2$)$_n$—S—X where:
X is —C(=Z)Y or —S—U;
Z is O or S;
each of Y and U is, independently, an alkyl, aryl or saccharide group optionally substituted with an OH, SH, or NH group;
n is 1 to 4; and
Nu is a nucleoside which comprises a ribose or deoxyribose sugar portion covalently bound to a base portion.

2. The compound of claim 1 wherein X is —S—U and U is —(CH$_2$)$_{n1}$—X$^1$ where X$^1$ is H, OH, SH or NH$_2$ and n$^1$ is 1–4.

3. The compound of claim 2 wherein R is —(CH$_2$)$_2$—S—S—(CH$_2$)$_2$—OH.

4. The compound of claim 1 wherein X is —C(=Z)Y and Y is CH$_3$ or tBu.

5. The compound of claim 4 wherein R represents —(CH$_2$)$_n$—S—C(=O)—CH$_3$ or (CH$_2$)$_n$—S—C(=O)-tBu with n=1 or 2.

6. A compound having the formula:

R—O—P(=O)(—O—R)—Nu wherein:
each R is, independently. —(CH$_2$)$_n$—S—X where:
X is —C(=Z)Y or —S—U;
Z is O or S;
each of Y and U is, independently, an alkyl, aryl or saccharide group optionally substituted with an OH, SH, or NH group;
n is 1 to 4; and
Nu is a 5' residue of a 2',3'-dideoxynucleoside or a 2',3'didehydronucleoside.

7. The compound of claim 6 wherein Nu is a 5' residue of dideoxyuridine, dideoxythymidine, dideoxycytidine, 3'-azido-2',3'-dideoxythymidine, or a derivative thereof which is substituted on a pyrimidine base portion or at positions 2' and 3' of said sugar portion.

8. A compound having the formula:

R—O—P(=O) (—O—R)—Nu wherein:
each R is, independently, —(CH$_2$)$_n$—S—X where:
X is —C(=Z)Y or —S—U;
Z is O or S;
each of Y and U is, independently, an alkyl, aryl or saccharide group optionally substituted with an OH, SH, or NH group:
n is 1 to 4; and
Nu is a carbonucleoside, a phosphonucleoside, or an acyclonucleoside.

9. The compound of claim 8 wherein Nu is a methoxyalkylpurine or a methoxyalkylpyrimidine or of formula CH$_2$—O—alkylpurine or CH$_2$—O—alkylpyrimidine.

10. The compound of claim 9 wherein Nu is a 3-hydroxy-2-methoxypropylpurine, a 3-hydroxy-2-methoxypropylpyrimidine, of formula —CH$_2$—OCH(CH$_2$OH)—CH$_2$-purine or —CH$_2$—O—CH(CH$_2$OH)—CH$_2$-pyrimidine, a 2-methoxyethylpurine, a 2-methoxyethylpyrimidine, or of formula —CH$_2$—O—C$_2$H$_4$-purine or —CH$_2$—O—C$_2$H$_4$-pyrimidine.

11. A process for preparing a compound of claim 1 wherein:
a compound of formula (II):

O$^-$—P(=O) (O$^-$)—Nu     (II)

is reacted with a compound of formula (III):

X—S—(CH$_2$)$_n$—OH     (III)

where X is protected, to provide a protected compound of claim 1; and
said protected compound of claim 1 is deprotected.

12. The process of claim 11 wherein said reaction between said compounds of formulas (II) and (II) takes place in the presence of a condensing agent in pyridine.

13. A compound having the formula:

R—O—P(=O)(—O—R)—Nu wherein:
each R is, independently, —(CH$_2$)$_n$—S—X where:
X is —C(=Z)Y or —S—U;
Z is O or S;
each of Y and U is, independently, an alkyl, aryl or saccharide group optionally substituted with an OH, SH, or NH group;
n is 1 to 4; and
Nu is a nucleoside.

* * * * *

UNITED STATES PATENT AND TRADEMARK OFFICE
CERTIFICATE OF CORRECTION

PATENT NO. : 5,770,725
DATED : June 23, 1998
INVENTOR(S) : Gosselin et al.

It is certified that error appears in the above-identified patent and that said Letters Patent is hereby corrected as shown below:

Col. 3, line 43, please insert "Y" before the word "appropriately".
Col. 11, line 24, please delete "dideoxynucleosid" and insert therefor --dideoxynucleoside--.
Col. 11, line 42, please delete "wash" and insert therefor --washed--.

Signed and Sealed this

Sixth Day of April, 1999

Q. TODD DICKINSON

Attest:

Attesting Officer

Acting Commissioner of Patents and Trademarks